United States Patent [19]
Kudo et al.

[11] Patent Number: 5,810,984
[45] Date of Patent: Sep. 22, 1998

[54] NITROGEN OXIDE SENSOR AND METHOD OF MANUFACTURING THE SENSOR

[75] Inventors: Shuzo Kudo; Hisao Ohnishi; Hisashi Sakai, all of Osaka, Japan

[73] Assignee: Osaka Gas Co., Ltd., Osaka, Japan

[21] Appl. No.: 837,746

[22] Filed: Apr. 22, 1997

[30] Foreign Application Priority Data

Apr. 24, 1996 [JP] Japan ................. 8-102148

[51] Int. Cl.$^6$ .................................. G01N 27/26
[52] U.S. Cl. ............... 204/426; 204/425; 204/427; 204/422; 204/83; 204/94; 204/98; 422/83; 422/94; 422/98; 505/121; 505/160; 505/451; 505/501; 436/116; 436/117; 436/118; 436/137; 427/124; 427/125; 427/126.3; 427/584; 427/585; 427/586; 73/23.2; 73/31.05; 73/31.06
[58] Field of Search .................. 505/121, 160, 505/451, 501, 450; 422/83, 90, 94, 98; 436/116–118, 136, 137; 73/23.2, 31.05, 31.06; 204/424–427, 429, 421; 427/124, 125, 126.3, 584–586

[56] References Cited

U.S. PATENT DOCUMENTS 4,701,739 10/1987 Sasaki ........................ 338/34
5,397,541 3/1995 Post ........................... 422/88
5,413,981 5/1995 Egawa et al. ................. 505/121

FOREIGN PATENT DOCUMENTS 0632265 1/1995 European Pat. Off. .

OTHER PUBLICATIONS

J.B. Mandal et al., Physica C, 1993, 216, pp. 195–198.
X.J. Huang et al., Solid State Ionics, 1994, 72, pp. 338–343.

*Primary Examiner*—Bruce F. Bell
*Attorney, Agent, or Firm*—Felfe & Lynch

[57] ABSTRACT

A nitrogen oxide sensor and a method of manufacturing the sensor are disclosed. The sensor has a gas detecting portion including sensitive material having electric property thereof subject to change in association with presence of nitrogen oxide in gas and a pair of electrodes electrically connected with the gas detecting portion. The gas detecting portion includes, as a main component thereof, metal oxide compound represented by a general formula:

$$Bi_2Sr_2(Ca_{1-x}Y_x)Cu_2O_{8+y}$$

$$(0.8 \leq x \leq 1;\ 0 \leq y \leq 1)$$

and having the 2212 phase crystal structure and crystalline size greater than 100 Å.

5 Claims, 5 Drawing Sheets

NITROGEN OXIDE SENSOR AND METHOD OF MANUFACTURING THE SENSOR

BACKGROUND OF THE INVENTION

1. Field of the Invention

The present invention relates to a nitrogen oxide sensor for detecting nitrogen oxide for such applications as the art of reducing or decomposing nitrogen oxide, and relates also to a method of manufacturing the sensor.

2. Description of the Related Art

As well-known, nitrogen oxides present in e.g. combustion exhaust gas generated from an internal combustion engine, boiler or the like are major cause of air pollution. Hence, there has been imminent need for development of sensor capable of measuring concentration of nitrogen oxides in the exhaust gas with high precision.

As such analyzer and sensor, there are known those based on the methods of chemiluminescence, infrared or UV absorbance, and controlled potential electrolysis. Further, as a sensor providing improvement over the above known sensors, there has been proposed a sensor using superconducting material in a detecting portion thereof.

In fact, as a sensor of the latter-mentioned type, the present inventors, Kudo et al., too have proposed a sensor using material represented by a following general formula:

$$Bi_2Sr_2(Ca_{1-x}Y_x)Cu_2O_{8+y}$$

$$(0.8 \leq x < 1; \ 0 \leq y \leq 1)$$

and having the 2212 phase crystal structure. This sensor provides superior sensitivity to nitrogen oxides as well as superior reversible sensitivity which is another essential requirement of sensor (Japanese patent application Hei. 5-160985).

In general, in order for a sensor to be of practical use, the sensor needs to meet three basic requirements as follow.

(1) sensitivity selectivity

The sensor needs to be highly sensitive to gas component to be detected (nitrogen oxide), and the sensor also needs to have good selectivity to be able to detect the target gas component as distinct from the other coexisting gas components.

(2) reversible sensitivity

Once having detected the target gas component, the sensor needs to be able to return to the zero-point, i.e. its original resistance, as quickly as possible when the concentration of the gas component becomes '0' (zero).

(3) durability

The sensor needs to provide reliably constant sensitivity through gas detecting or monitoring operation continued over an extended period of time.

Now, studying the performance of the above-proposed type of nitrogen oxide sensor in the above respects, while this sensor provides satisfactory performance in (1) and (2), it still has room for improvement in (3).

In view of the above, a primary object of the present invention is to provide a further improved nitrogen oxide sensor which is capable of meeting all of the three requirements, and to provide also a method of manufacturing such sensor.

SUMMARY OF THE INVENTION

According to one aspect of the present invention, there is provided a nitrogen oxide sensor, which comprises:

a gas detecting portion including sensitive material having electric property thereof subject to change in association with presence of nitrogen oxide in gas; and a pair of electrodes electrically connected with the gas detecting portion;

wherein the gas detecting portion includes, as a main component thereof, metal oxide compound represented by a general formula:

$$(Bi_2Sr_2(Ca_{1-x}Y_x)Cu_2O_{8+y}$$

$$(0.8 \leq x \leq 1; \ 0 \leq y \leq 1)$$

and having the 2212 phase crystal structure and crystalline size greater than 100 Å.

The "crystalline size" referred to above is a value determined by the so-called Wilson method. It should be noted, however, that the specific type of method of this crystalline size measurement is not particularly limited in the present invention. If the crystalline size determined by whatever method available fits within the above-specified range, then, the object, function and effect of the invention can be achieved as will be described next.

(1) sensitivity selectivity

Concerning the metal oxide compound represented by the above formula, FIG. 1 graphically illustrates change in the sensitivity which occurs in association with variation in the ratio between Ca and Y in the above-specified formula. In this figure, the horizontal axis represents the ratio of Y, while the vertical axis represents the sensor sensitivity (specifically, a resistance value R for air containing 2500 ppm of NO/a resistance value $R_0$ for air alone). Except for the formula, the metal oxide compound employed in this test satisfies the other features of the present invention.

As may be apparent from this figure, the material having Y in the ratio range between 0.8 and 1.0 (i.e. x=0.8 to 1.0) is preferred as achieving superior sensitivity.

Next, by using the material of the above formula having Y in the ratio of 1.0 as an example, the selectivity tendency will be discussed with reference now to FIGS. 2 and 3.

FIG. 2 illustrates the results obtained from material having crystalline size about 600 Å, and FIG. 3 illustrates the results obtained from material having crystalline size about 80 Å, respectively.

In both of these figures, the horizontal axis represents the gas component concentration and the vertical axis represents the sensitivity thereto. The kinds of gas employed are denoted with marks. From these, it may be understood that the material of the invention is capable of selectively detecting the target gas component as distinct from the other coexisting gas components.

2) reversible sensitivity

Reversible sensitivity, i.e. the ability to quickly return to the original resistance, is affected significantly by the crystal structure. FIG. 4(a) shows the reversible sensitivity of the material of the invention comprised mainly of the 2212 phase, while FIG. 4(b) shows that of reference material including other phases ($Y_2Cu_2O_5$, $SrBi_2O_4$, $Sr_3Bi_2O_6$) in abundance.

In these figures, the horizontal axis represents time and the vertical axis represents the resistance value corresponding to the sensor sensitivity. Further, in these examples, nitrogen monoxide (NO) and nitrogen dioxide ($NO_2$) were employed as the nitrogen oxides. In this respect, it should be noted however that nitrogen monoxide and nitrogen dioxide equilibrate with each other and hence that confirmation of ability to detect nitrogen monoxide may be considered to be equivalent to confirmation of ability to detect nitrogen oxide.

Within the range: x=0.8 to 1.0, substantially same results were obtained. It was found that the crystalline size die not significantly affect the reversible sensitivity within the time span shown.

Hence, it may be understood that the compound comprised mainly of the 2212 phase is superior in the reversible sensitivity as least within the shorter time span (i.e. recoverability upon each detection).

3) durability

From the above taken together, it may be concluded that the compound having the formula: x=0.8 to 1.0 and the 2212 phase crystal structure well suits the object of the present invention. Next, the compound having these features will be further described in terms of durability, i.e. performance over a longer period of time.

In the following evaluation of durability, a new concept referred to herein as 'sensitivity change rate', based on the following expression, was introduced. Namely;

$C = Rs_{1500}/Rs_0$ where,

C=sensitivity change rate $Rs_{1500}$=sensitivity value to nitrogen oxide after lapse of 1,500 hours, and $Rs_0$=original sensitivity value to nitrogen oxide at the beginning of test.

The test results of this sensitivity change rate are shown in FIGS. 5, 6, 7 and 8.

In these figures, the horizontal axis represents the crystalline size (Å) and the vertical axis represents the sensitivity change rate described above.

FIGS. 5, 6, 7 and 8 show the results when the ratio of Y relative to Ca was varied and which correspond respectively to the compounds of x=1.0, 0.9, 0.8 and 0.0, respectively. Hence, FIG. 5 corresponds to the compound having only Y and FIG. 8 corresponds to the compound having only Ca.

Referring to these results, it may be seen that the sensitivity change rate is dependent on the crystalline size and that the material having the crystalline size greater than 100 Å achieved the distinguished sensitivity change rate of 0.8 to 0.9 or more approximately. Thus, for better sensor durability, the crystalline size should be greater than 100 Å.

Now, the compound having the crystalline size greater than 100 Å provides good performance in durability as described above. In confirming this, however, the confirmation was made only to 600 Å, which is the physical limit inherent in the Wilson method. In the above range, good results were obtained.

Preferably, the gas detecting portion further includes inactive metal oxide which does not chemically react with the nitrogen oxide. With this addition, the physical strength of the gas detecting portion may be improved. The 'inactive metal oxide' referred to above represents any metal oxide which is free from an irreversible reaction, especially, chemical reaction, with the nitrogen oxide. Examples of such inactive metal oxide are $SiTiO_2$, $MgO$ and $Al_2O_3$.

Preferably, the gas detecting portion further includes, at least on a surface side thereof, an oxidation catalyst layer carrying platinum. With this addition of catalyst layer, the selectivity to nitrogen oxide may be further enhanced.

Preferably, the ratio of the 2212 phase satisfies at least one of the following conditions (a), (b), (c) and (d), Namely;

(a) $\Sigma I[2212]/\Sigma I[T]>88.1\%$ (b) $\{\Sigma I[2212]+\Sigma I[2201]\}/\Sigma I[T]>94.8\%$ (c) $\{\Sigma I[2212]+\Sigma I[Y_2O_3]\}/\Sigma I[t]>88.1\%$ (d) $\{\Sigma I[2212]+\Sigma I[(Bi, Ca)O]\}/\Sigma I[T]>88.8\%$ where, $\Sigma I[2212]$ denotes sum of diffraction peak intensities based on the 2212 phase, $\Sigma I[2201]$ denotes sum of diffraction peak intensities based on the 2201 phase, $\Sigma I[Y_2O_3]$ denotes sum of diffraction peak intensities based on $Y_2O_3$, $\Sigma I[(Bi, Ca)O]$ denotes sum of diffraction peak intensities based on oxide including one or both of Bi and Ca and not including any other metal, $\Sigma I[T]$ denotes sum of diffraction peak intensities based on oxide including at least one selected from the group consisting of Bi, Sr, Ca, Y and Cu.

When any one of the above conditions is satisfied, it follows that the gas detecting portion is constituted mainly from the 2212 phase, thus achieving the above-described advantageous effects.

According to a further aspect of the present invention, there is provided a method of manufacturing a nitrogen oxide sensor having a gas detecting portion including sensitive material having electric property thereof subject to change in association with presence of nitrogen oxide in gas and a pair of electrodes electrically connected with the gas detecting portion, wherein, for manufacturing the gas detecting portion, the method comprises the steps of:

depositing step for forming a deposited layer of material represented by a general formula:

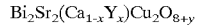

$Bi_2Sr_2(Ca_{1-x}Y_x)Cu_2O_{8+y}$ $(0.8 \leq x \leq 1; \ 0 \leq y \leq 1)$; and heating step of heating the deposited layer at 920° to 250° C. to obtain the gas detecting portion including as a main component thereof metal oxide compound represented by said general formula and having the 2212 crystal structure and crystalline size greater than 100 Å.

In the above method of manufacturing a nitrogen oxide sensor, starting material and other raw material of predetermined compositions are prepared in advance, and the deposited layer of this starting material is formed in the depositing step. For effecting this depositing step, depositing and film forming operation on the plate using the laser ablation method, IBS method, RF sputtering method, MBE method, MOCVD method and so on may be used, for example. In this respect, the deposited layer may be either in the crystalline or non-crystalline state. That is, the layer may be of crystalline structure having extremely small grain size (crystalline size), or the layer may also be of non-crystalline structure.

After obtaining the deposited layer described above, the heating step is effected for adjusting the crystal structure and crystalline size (in practice, for making the size greater than 100 Å). With these, there may be obtained a nitrogen oxide sensor having a gas detecting portion with the advantageous properties described hereinbefore.

In the above heating step, it is preferred that the heating temperature range between 920° and 950° C. If the heating temperature is below this range, the resultant gas detecting portion may not be formed mainly of the 2212 phase or the crystalline size will tend to be smaller than 100 Å. Conversely, if the temperature is higher than the above range, the detecting portion may not be formed mainly of the 2212 phase.

In the above description, the step of forming the deposited layer and the heating step are described as two seemingly separate steps to be effected on after the other. However, these phenomena of layer formation and crystal structure development and size adjustment may take place not so distinctly from each other. In fact, in some cases, these phenomena appear to take place simultaneously. Specifically, in the case of the laser ablation operation, for instance, it is conceivable to maintain the plate, which is disposed in opposition to the target, at a relatively high temperature, so as to promote the crystallization in the deposited layer deposited on the plate, simultaneously with the ablation operation.

In the above, in the case of the laser ablation method if employed, this method is inherently capable of providing sufficient film forming energy to the material. Then, with setting the film forming temperature to 750° to 950° C., the gas detecting portion comprised mainly of the metal oxide compound having the 2212 phase crystal structure and the crystallin size greater than 100 Å may be obtained.

Further and other objects, features and effects of the invention will become more apparent from the following more detailed description of the embodiments of the invention with reference to the accompanying drawings.

DETAILED DESCRIPTION OF THE PREFERRED EMBODIMENTS

Now, preferred embodiments of the present invention will be particularly described with reference to the accompanying drawings, in the order of: sensor construction, method of manufacturing the sensor, measurement method using the sensor and sensor characteristics.

Figure 1:
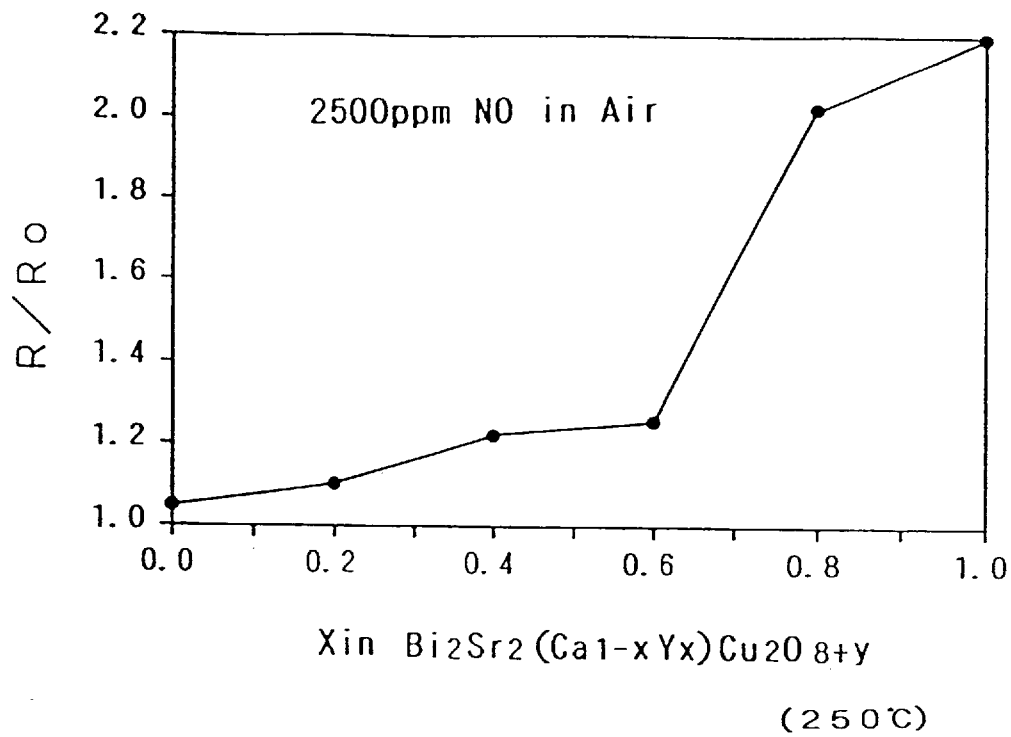
FIG. 1 is a graph showing nitrogen oxide sensitivity property of Bi—Sr—Ca—Y—Cu—O system.
Figure 2:
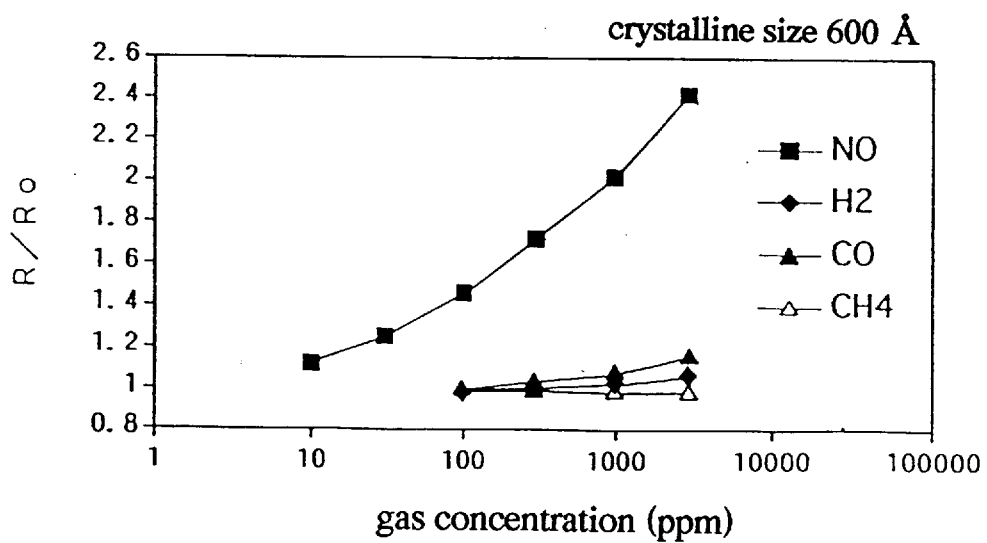
FIG. 2 is a graph showing selectivity of a sensor including a gas detecting portion having a large crystalline size.
Figure 3:
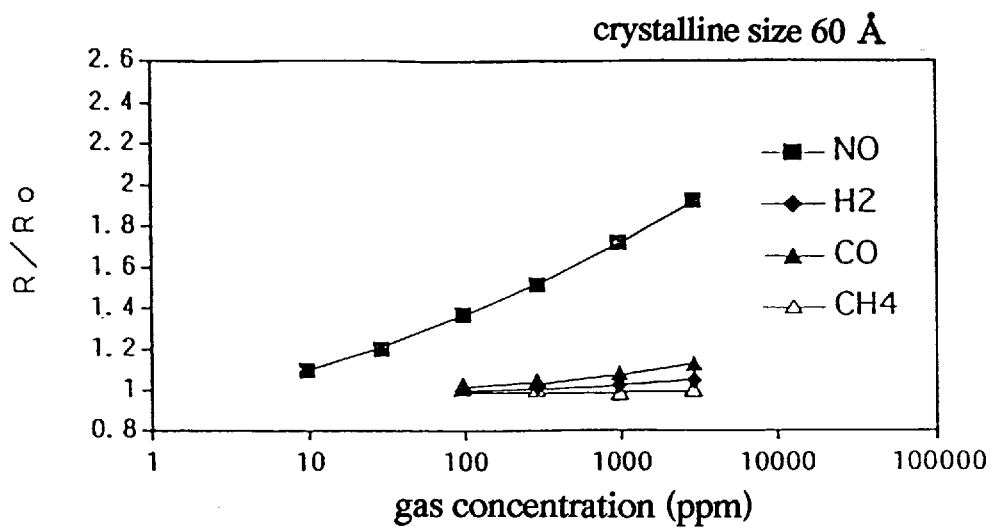
FIG. 3 is a graph showing selectivity of a further sensor including a gas detecting portion having a small crystalline size.
Figure 4:
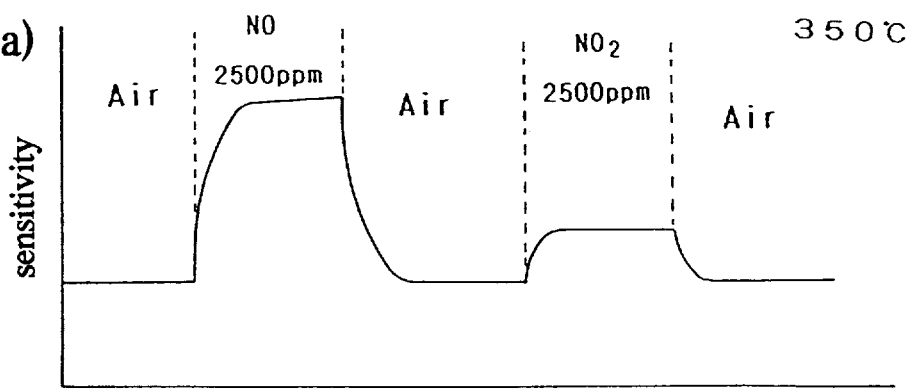
FIGS. 4a and 4b are graphs illustrating correlation between crystal structure and reversible sensitivity.
Figure 4:
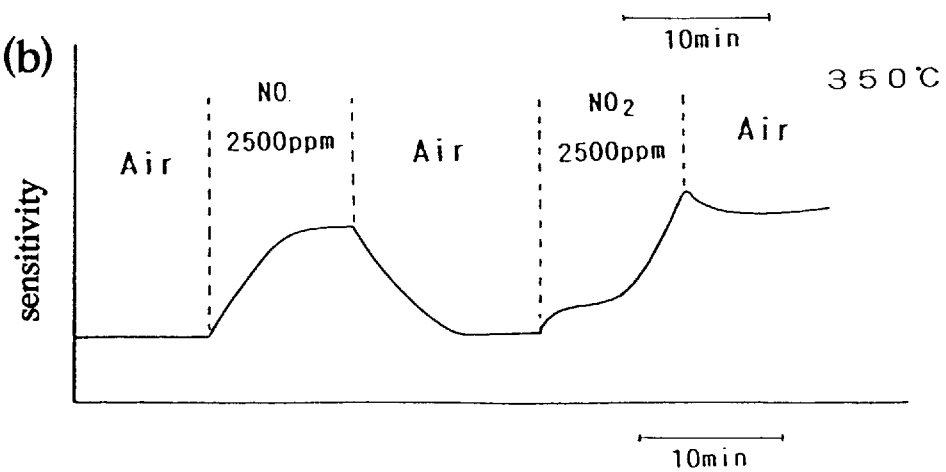
Figure 5:
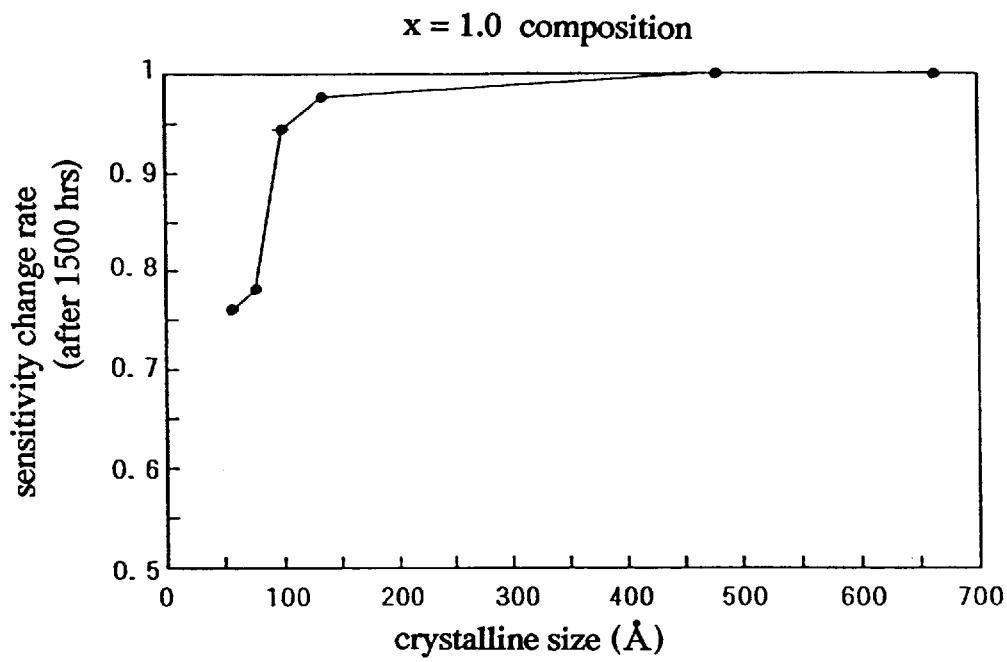
FIG. 5 is a graph illustrating correlation between crystalline size and sensitivity change rate of a system having its Y component entirely substituted.
Figure 6:
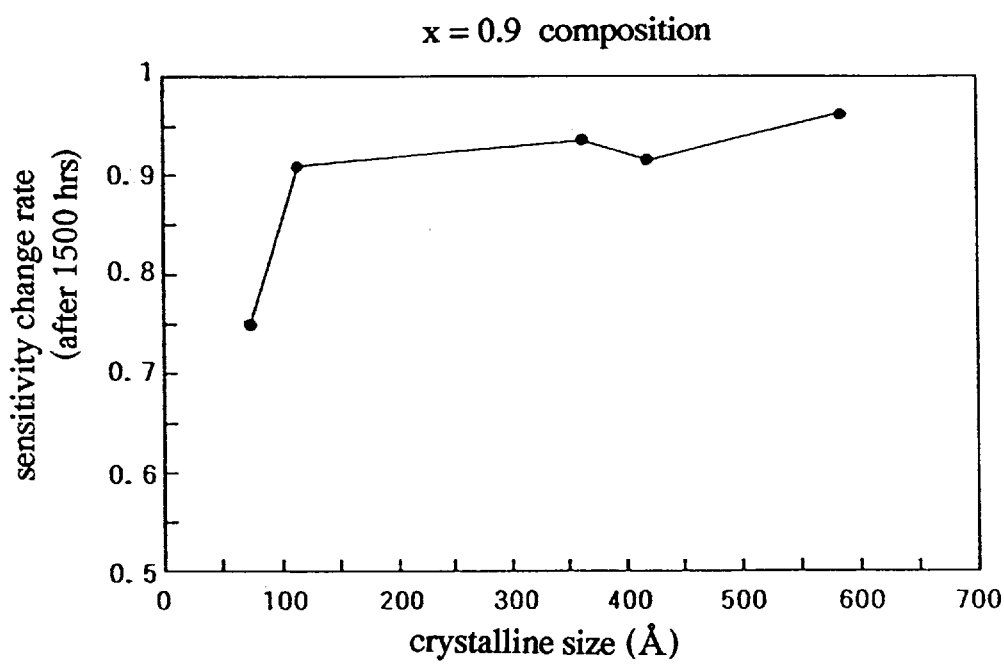
FIG. 6 is a graph illustrating correlation between crystalline size and sensitivity change rate of a further system including Y component at a ratio of 0.9.
Figure 7:
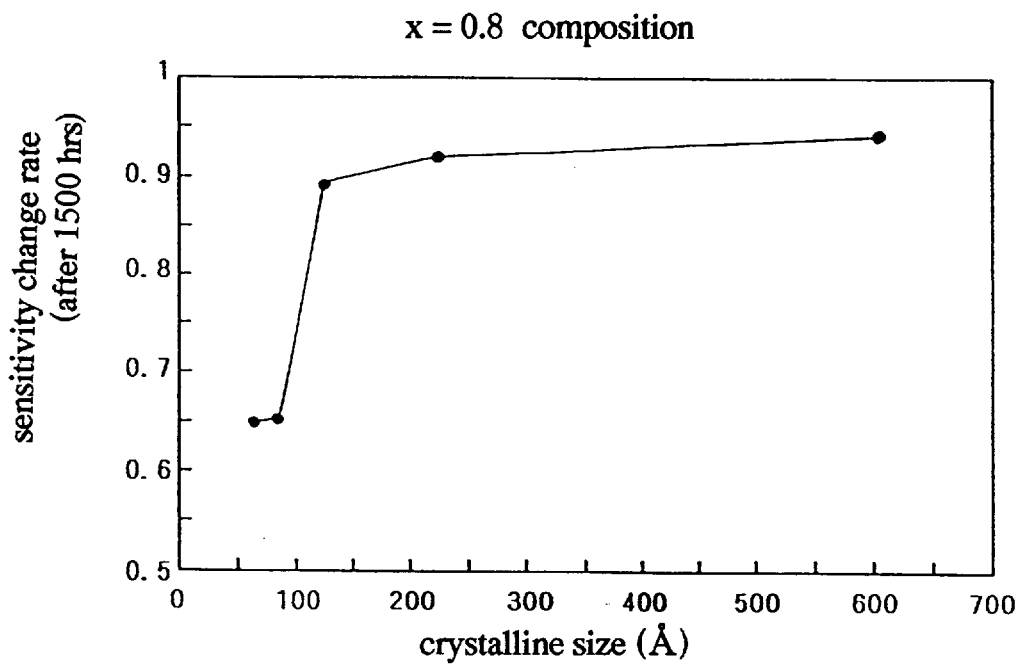
FIG. 7 is a graph illustrating correlation between crystalline size and sensitivity change rate of a still further system including Y component at a ratio of 0.8.
Figure 8:
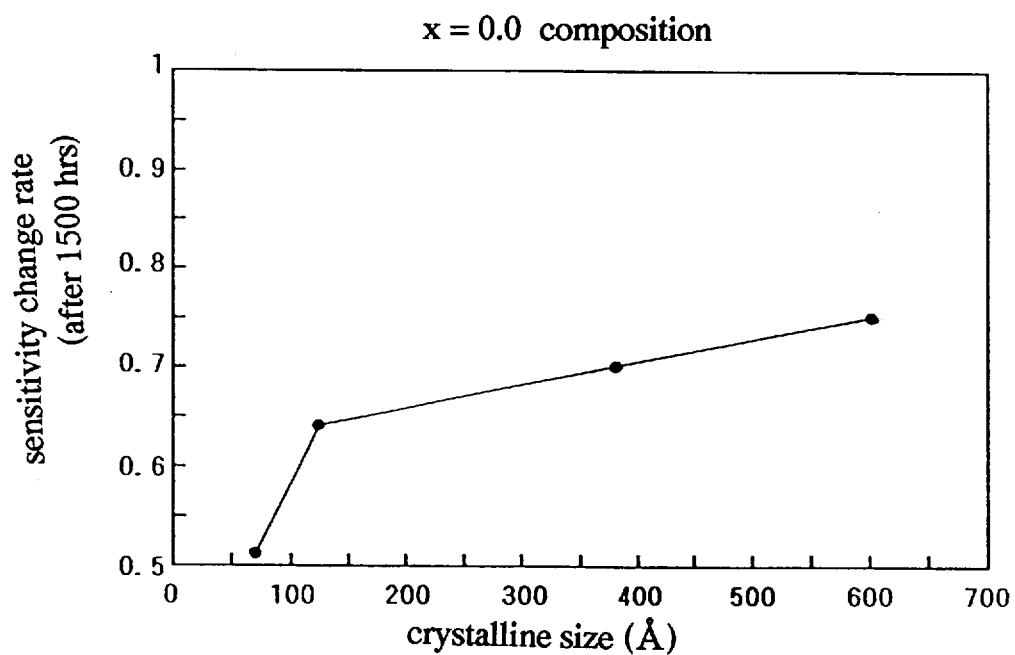
FIG. 8 is a graph illustrating correlation between crystalline size and sensitivity change rate of a still further system including Y component at a ratio of 0.0.
Figure 9:
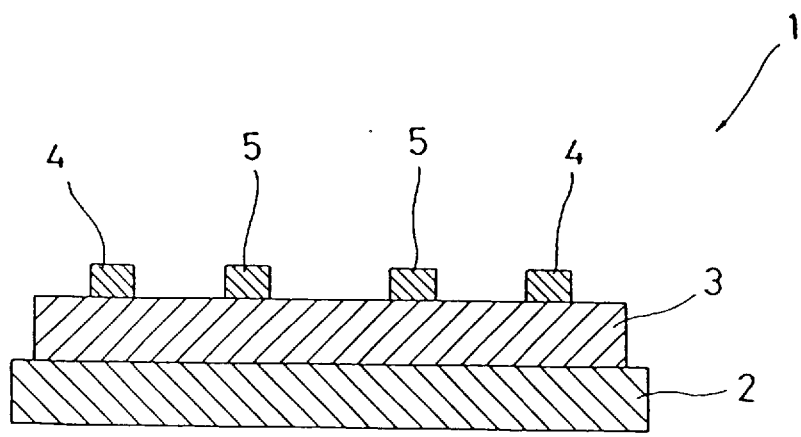
FIG. 9 is a schematic construction view of a nitrogen oxide sensor according to one preferred embodiment of the invention.

(1) sensor construction:

FIG. 9 shows the construction of a nitrogen oxide sensor according to one embodiment of the invention. This sensor 1 includes a heating plate 2 comprising a ceramic heater plate and a gas detecting portion 3 disposed on the plate, and a pair of current applying platinum electrodes 4 and a pair of potential detecting platinum electrodes 5 attached to the gas detecting portion 3. The gas detecting portion 3 is in the form of thin film and formed of metal oxide compound specified by the present invention, i.e. having the composition represented by a general formula:

$$Bi_2Sr_2(Ca_{1-x}Y_x)Cu_2O_{8+y}$$

$$(0.8 \leq x \leq 1; 0 \leq y \leq 1).$$

To the metal oxide compound employed in this gas detecting portion 3, nitrogen oxide can be reversibly adsorbed. So that, the detecting portion 3 provides different electric resistance values between the condition when the nitrogen oxide is adsorbed thereto and the further condition when no nitrogen oxide is adsorbed thereto. The amount of this change in the resistance value corresponds to the amount of adsorbed nitrogen oxide, i.e. the concentration of the nitrogen oxide present in the gas to which the detecting portion is exposed.

(2) method of manufacturing the sensor 1) manufacture of the gas detecting portion 3:

The method of manufacturing the gas detecting portion 3 will be described next, with taking for example the material of x=1 in the above formula.

[first step]

Precursor material is obtained from raw mixture material including, in a predetermined equivalent ratio, essential elements for forming the sensitive material to be used in the gas detecting portion 3.

Particularly, as the metal oxide compound has the above-specified formula, raw materials are mixed in such a manner as to obtain the metal components (Bi: Sr: Y: Cu) substantially in the predetermined equivalent ratio of: (2:2:1:2). Examples of the raw materials to be mixed to obtain Bi: Sr: Y: Cu are $Bi_2O_3$, $SrCO_3$, $Y_2O_3$, CuO, respectively.

[second step]

Preliminary baking and sintering is effected on the precursor material obtained as above, whereby preliminary sintered product is obtained.

More particularly, in this preliminary sintering step, the precursor material is sintered at a lower temperature (780° to 800° C. approximately) than that employed in a main sintering step to be described later for a period of 24 hours or longer, preferably 48 hours approximately. The resultant preliminary sintered produce is pulverized to adjust its particle diameter to 1 to 20 µm approximately.

[third step]

The pulverized and size-adjusted preliminary sintered produce obtained as above is then subjected to at least two cycles of main sintering steps at a temperature range of 815° to 848° C. (T1) in noble gas or nitrogen gas atmosphere containing 20% or more of oxygen.

As a result, there is obtained laser ablation target comprised mainly of metal oxide compound represented by the formula:

$$Bi_2Sr_2Y\ Cu_2O_{8+y}$$

$$(0 \leq y \leq 1)$$

and having the 2212 phase crystal structure. Incidentally, in the above-described main sintering step, the material is again pulverized to adjust its particle diameter to 1 to 20 µm approximately.

For the sintering atmosphere, noble gas such as argon gas, helium gas or nitrogen gas is employed. Each cycle of main sintering step is effected at the above-specified temperature range (T1) and for a period of 24 hours or longer.

More preferably, the main sintering step is effected for at least two cycles within argon gas atmosphere containing 20% or more of oxygen at a temperature range of 820° to 845° C. (T2) for a period longer than 30 hours.

In summary, in the case of the laser ablation method, the target for the laser ablation is obtained by: the step of obtaining the precursor material from the raw mixture material having the essential components for the target in the predetermined equivalent ratio (i.e. the ratio represented by the general formula above); the preliminary sintering step for effecting preliminary sintering on the precursor material to obtain preliminary sintered product, and the step of subjecting the preliminary sintered product to at least two cycles of main sintering step at the temperature range of 815° to 848° C.

[fourth step]

Next, the target obtained as above is subjected to the laser ablation to obtain, on the plate, a film formed of non-crystalline material having the above-specified formula. This film is formed in the thickness of 1 to 5 μm approximately.

laser type: KrF excimer laser laser wavelength: 248 nm plate temperature: 100° to 400° C.

atmosphere gas: oxygen atmosphere pressure: $10^{-4}$ to $10^{-1}$ Torr irradiation energy density: 3 J/cm$^2$ laser oscillation frequency: 5 to 10 Hz plate type: SrTiO$_3$, MgO, or the like target-substrate distance: 3.5 to 7.0 cm

[fifth step]

The non-crystalline material film formed on the plate is then heated at 920° to 950° C. for a period of 20 to 60 minutes. After this heating treatment, there is consequently obtained the gas detecting portion 3 comprised mainly of the material having the 2212 phase crystal structure and the crystalline size greater than 100 Å.

Figure 10:
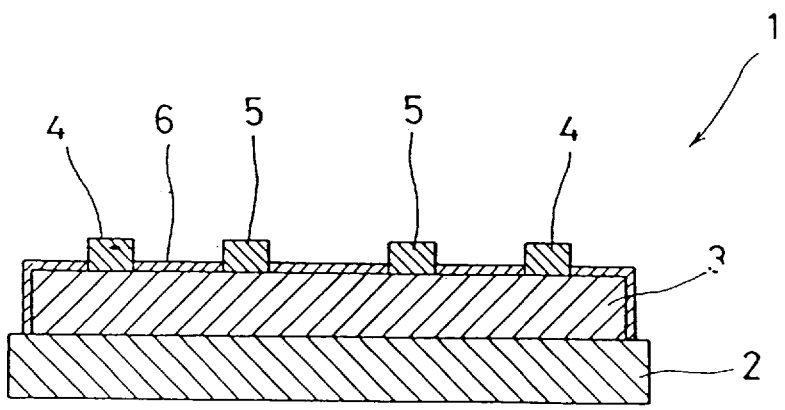
FIG. 10 is a schematic construction view of a nitrogen oxide sensor according to a further embodiment.

2) method of manufacturing the sensor:

To the upper face of the gas detecting portion 3 obtained in the manner described above, the electrodes 4, 5 are attached and also the heating plate 2 is attached to the bottom face of the plate mounting the gas detecting portion thereon. Then, a measuring unit and a control unit (not shown) are connected to the above assembly, whereby the sensor is completed. Further, if necessary and as a further embodiment, an oxidation catalyst layer 6 carrying platinum may be attached to the surface of the gas detecting portion 3, as illustrated in FIG. 10.

(3) measurement method using the sensor and sensor characteristics:

Determination of the characteristics of the nitrogen oxide sensor manufactured as above is carried out as follows.

A predetermined potential is applied to the heating plate 2 to heat the gas detecting portion 3 to 250° to 450° C., and a predetermined current is applied to the current applying electrodes 4. Under these conditions, the sensor is exposed to gas containing a predetermined concentration of nitrogen oxide in the air. And, a potential is obtained from the potential detecting electrodes 5 and an electric resistance developed in the gas detecting portion is obtained.

According to experiments conducted in the above-described manner, the sensor having the above construction achieved the afore-described distinguished performance tendency in the sensitivity, selectivity, reversible sensitivity and durability. A control sensor having up to 20% of Ca substituted for by Y in the above-described formula achieved substantially the same performance as well.

As a result, there has been obtained a practical and useful nitrogen oxide sensor which is satisfactory in all of the sensor requirements of sensitivity, selectivity, reversible sensitivity and durability.

[other embodiments]

Other embodiments of the present invention will be described next.

(A) In the foregoing embodiment, the gas detecting portion is provided in the form of thin film. Instead, this portion may be provided in the form of sintered body. Though may be inferior in the sensitivity performance in comparison with the film type detecting portion, the sintered body type gas detecting portion too can achieve substantially same durability performance, substantially free from deterioration in the sensitivity change rate over an extended period of time. As for the reversible sensitivity, it is preferred that the crystal structure be formed mainly of the 2212 phase. Further, for better durability performance, the crystalline size should be greater than 100 Å.

(B) in the foregoing embodiment, as the film forming method, the laser ablation method is employed. Instead, any other method may be employed as long as it allows deposition of the material having the target composition on the substrate.

Specifically, the MBM method, IBS method, RF sputtering method, MOCVD method or the like may be employed also.

(C) In the foregoing embodiment, after the non-crystalline film is formed on the plate (fourth step), the film is heated to obtain the metal oxide compound having the predetermined crystalline size. However, in the method of the present invention, there are no limitations concerning these processes.

For instance, for the same purpose, any of following three methods may be employed also.

C-1: post-annealing method

In this method, as described hereinbefore, in the film forming step, the film is first deposited in the form of non-crystalline material film. Then, this film is heated to develop crystal structure therein.

C-2: as-deposition method

In this method, deposition and the crystallization of the metal oxide compound are carried out simultaneously, by heating the substrate to a high temperature (750° to 950° C.) during the film formation. In this method, the laser ablation method is generally employed. The other conditions of the laser ablation may be identical to those of the foregoing. This method is of high practical value.

C-3: annealing after as-deposition method

In this case, the film formed by the above-described as-deposition method is again heated to develop therein the crystal structure having a crystalline size greater than a predetermined value.

Any of the above-described methods and still other methods may be employed. Yet, basically, after forming the film of the target composition (including both non-crystal and partially crystal condition), then, by heating this film at 920° to 950° C. for 20 to 60 minutes, the target product of the invention may be obtained.

(D) In the foregoing embodiment, the material forming the gas detecting portion may further include inactive metal oxide such as SiTiO$_3$, MgO, Al$_2$O$_3$ or the like, which does not chemically react with the nitrogen oxide. This may improve the physical strength of the gas detecting portion.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which come within the meaning and range of equivalency of the claims are therefore intended to be embraced therein.

We claim:

1. A nitrogen oxide sensor comprising:

a gas detecting portion including sensitive material having electric property thereof subject to change in association with presence of nitrogen oxide in gas; and a pair of electrodes electrically connected with the gas detecting portion;

wherein the gas detecting portion includes, as a main component thereof, metal oxide compound represented by a general formula:

$$Bi_2Sr_2(Ca_{1-x}Y_x)Cu_2O_{8+y}$$

$(0.8 \leq x \leq 1; 0 \leq y \leq 1)$ and having the 2212 phase crystal structure and crystalline size greater than 100 Å.

2. A nitrogen oxide sensor as defined in claim 1, wherein the gas detecting portion further includes inactive metal oxide which does not chemically react with the nitrogen oxide.

3. A nitrogen oxide sensor as defined in claim 1 or 2, wherein the gas detecting portion includes, at least on a surface thereof, an oxidation catalyst layer carrying platinum.

4. Method of manufacturing a nitrogen oxide sensor having a gas detecting portion including, as a main component thereof, sensitive material having electric property thereof subject to change in association with presence of nitrogen oxide in gas and a pair of electrodes electrically connected with the gas detecting portion, wherein, for manufacturing the gas detecting portion, the method comprises the steps of:

deposing step for forming a deposited layer of material represented by a general formula:

$$Bi_2Sr_2(Ca_{1-x}Y_x)Cu_2O_{8+y}$$

$(0.8 \leq x \leq 1; 0 \leq y \leq 1)$; and heating step of heating the deposited layer at 920° to 950° C. to obtain the gas detecting portion including as a main component thereof metal oxide compound represented by said composition and having the 2212 crystal structure and crystalline size greater than 100 Å.

5. Method of manufacturing a nitrogen oxide sensor having a gas detecting portion including, as a main component thereof, sensitive material having electric property thereof subject to change in association with presence of nitrogen oxide in gas and a pair of electrodes electrically connected with the gas detecting portion, wherein, the laser ablation method is employed, with setting a film forming temperature at 750° to 950° C., for obtaining the gas detecting portion comprised mainly of metal oxide compound represented by a general formula:

$$Bi_2Sr_2(Ca_{1-x}Y_x)Cu_2O_{8+y}$$

$(0.8 \leq x \leq 1; 0 \leq y \leq 1)$; and having the 2212 phase crystal structure and crystalline size greater than 100 Å.

* * * * *

UNITED STATES PATENT AND TRADEMARK OFFICE
CERTIFICATE OF CORRECTION

PATENT NO. : 5,810,984
DATED : September 22, 1998
INVENTOR(S) : Kudo et al.

It is certified that error appears in the above-identified patent and that said Letters Patent is hereby corrected as shown below:

In column 2, line 42, change "80 Å" to --60 Å--.

In column 3, line 2, change "die" to --did--.

In column 4, line 33, change "250°" to --950°--.

In column 6, line 44, change "produce" to --product--.

Signed and Sealed this

Third Day of August, 1999

Attest:

Q. TODD DICKINSON

Attesting Officer

Acting Commissioner of Patents and Trademarks